United States Patent
Wolff et al.

(10) Patent No.: US 10,101,316 B2
(45) Date of Patent: Oct. 16, 2018

(54) APPARATUS AND METHOD FOR DETERMINING DISTRIBUTION VOLUME IN DIALYSIS PATIENT

(71) Applicant: B. BRAUN AVITUM AG, Melsungen (DE)

(72) Inventors: Henrik Wolff, Witzenhausen (DE); Joern Meibaum, Baunatal (DE); Christof Strohhoefer, Kassel (DE)

(73) Assignee: B. BRAUN AVITUM AG, Melsungen (DE)

( * ) Notice: Subject to any disclaimer, the term of this patent is extended or adjusted under 35 U.S.C. 154(b) by 699 days.

(21) Appl. No.: 14/667,124

(22) Filed: Mar. 24, 2015

(65) Prior Publication Data

US 2015/0285782 A1    Oct. 8, 2015

(30) Foreign Application Priority Data

Apr. 3, 2014  (DE) .................. 10 2014 104 768

(51) Int. Cl.

| | |
|---|---|
| *A61M 37/00* | (2006.01) |
| *G01N 33/487* | (2006.01) |
| *G01F 1/00* | (2006.01) |
| *A61M 1/16* | (2006.01) |

(52) U.S. Cl.
CPC ..... *G01N 33/48785* (2013.01); *A61M 1/1609* (2014.02); *G01F 1/00* (2013.01); *A61M 2205/3306* (2013.01); *A61M 2205/3334* (2013.01)

(58) Field of Classification Search
CPC .......... G01N 33/48785; A61M 1/1609; A61M 2205/3306; A61M 2205/3334; G01F 1/00

USPC ................................................ 604/4.01–6.11
See application file for complete search history.

(56) References Cited

U.S. PATENT DOCUMENTS

| 6,258,027 B1 * | 7/2001 | Sternby .................. A61M 1/16 |
| | | 210/646 |
| 7,077,819 B1 | 7/2006 | Goldau et al. |
| 2007/0027402 A1 | 2/2007 | Levin et al. |

FOREIGN PATENT DOCUMENTS

| DE | 694 06 253 | 4/1998 |
| DE | 693 24 471 | 12/1999 |
| DE | 698 34 034 | 8/2006 |
| EP | 0 986 410 | 3/2000 |
| EP | 1 037 681 | 9/2000 |
| EP | 1 062 960 | 12/2000 |

(Continued)

OTHER PUBLICATIONS

European Search Report for EP 15158666.6 dated Aug. 25, 2015.

(Continued)

*Primary Examiner* — Philip R Wiest
(74) *Attorney, Agent, or Firm* — RatnerPrestia

(57) ABSTRACT

Apparatus and control methods for determining a distribution volume of at least one uremic substance in a dialysis patient are disclosed. The apparatus may include a dialyzer, an optional flow rate measuring system for detecting the flow rate of a dialysis fluid through the dialyzer, a dialysis fluid measuring system for detecting at least one dialysis fluid parameter that depends on the at least one substance in the dialysis fluid, and a computer for establishing a dialysis dose based on the dialysis fluid parameter and for establishing the distribution volume based on the dialysis dose taking a clearance factor and dialysis duration into account.

22 Claims, 1 Drawing Sheet

(56) References Cited

FOREIGN PATENT DOCUMENTS

| EP | 1 698 360 | 9/2006 |
|---|---|---|
| WO | WO 98/55166 | 12/1998 |
| WO | WO 99/29355 | 6/1999 |
| WO | WO 2010/043381 | 4/2010 |

OTHER PUBLICATIONS

Lopot, et al., "Continuous Blood Volume Monitoring and "Dry Weight" Assessment," J. Renal Care, 2007, Apr.-Jun.; 33(2), pp. 52-58.
Rodriguez et al., "Assessment of dry weight by monitoring changes in blood volume during hemodialysis using Crit-Line," Kidney International (2005) 68, pp. 854-861.
German Search Report for DE 10 2014 104 768.0 dated Feb. 23, 2015.
J.T. Daugirdas, "Second Generation Logarithmic Estimates of Single-Pool Variable Volume Kt/V: An Analysis of Error," J. Am. Soc. Nephrol., 1993, Fol. 4, pp. 1205-1213.

* cited by examiner

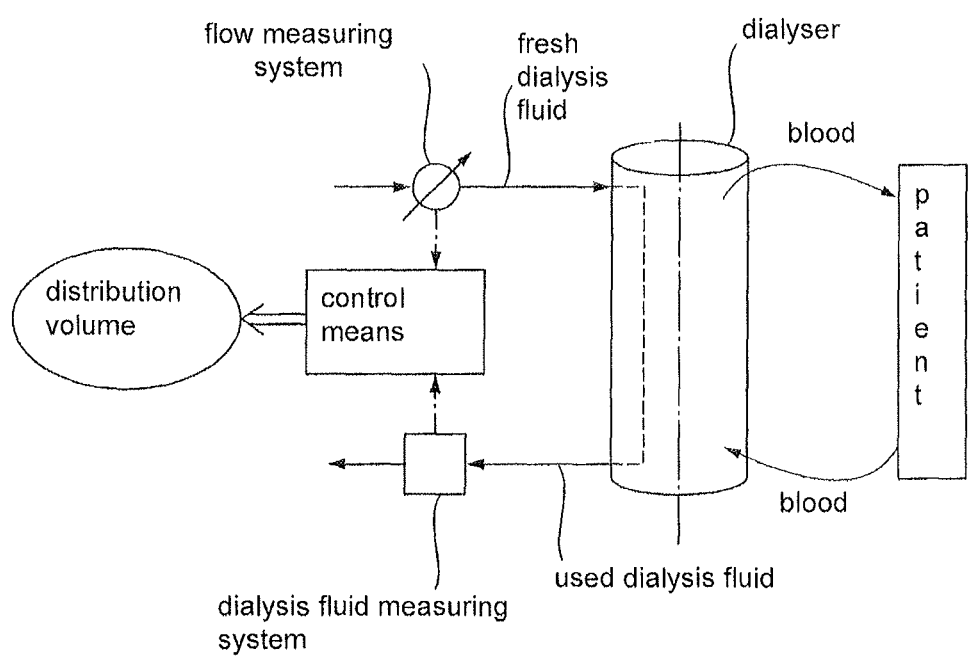

APPARATUS AND METHOD FOR DETERMINING DISTRIBUTION VOLUME IN DIALYSIS PATIENT

CROSS REFERENCE TO RELATED APPLICATIONS

This application claims priority to German application DE 10 2014 104 768.0 filed Apr. 3, 2014, the contents of such application being incorporated by reference herein.

FIELD OF THE INVENTION

The invention relates to an apparatus and a method for determining a distribution volume of at least one uremic substance in a dialysis patient.

BACKGROUND

In the period free from dialysis, apart from uremic substances an additional fluid volume accumulates in the dialysis patient. Apart from removing uremic substances, it is the function of the dialysis therapy to withdraw such fluid amount. This process is referred to as ultrafiltration. The fluid amount to be withdrawn is resulting from the difference of the patient's weight at the beginning of the dialysis treatment and a medically defined dry weight, namely, the weight of the patient without hyperhydration. The fluid volume of the body in which urea, the most prominent representative of small-molecular substances usually eliminated with the urine, is distributed is referred to as urea distribution volume. The urea distribution volume is approximately similar to the body fluid volume. At the beginning of treatment, this volume is composed of the "dry volume", the fluid volume of a dialysis patient with the medically established dry weight, and the volume accumulated in the period free from dialysis. Hence it is increased by the same value as the dry weight of the patient. Thus the urea distribution volume constitutes an important parameter for monitoring the fluid state and the general condition of the patient. At present, appropriate measuring techniques are missing for determining the urea distribution volume during treatment.

DESCRIPTION OF THE RELATED ART

For judging the dehydration result during the treatment several methods are available. In various cases bioimpedance measurements are used for monitoring the fluid state of the patient by means of analysis of the "body impedance" at typically 50 kHz. From US 2007/0027402 A1 a bioimpedance measuring method is known in which AC having plural frequencies is guided through at least two points on the skin, the voltage drop is detected for each frequency on at least two further points and the recorded voltage drop values are evaluated for different frequencies so as to derive at least one numerical value for muscle, fat and extracellular fluid.

From WO 2010/043381 A2 the monitoring of the hydration and/or nutrition state of a patient with the aid of bioimpedance measuring values is known. The respective method comprises the steps of: measuring bioimpedance data on the patient at the time t, determining a volume compartment of the patient by way of the bioimpedance data measured, determining the corrected volume compartment by multiplying the volume compartment or a variable correlated thereto by a factor k characteristic of the missing member or parts thereof.

However, measurement by means of bioimpedance measurement is complex and requires additional measuring systems which are moreover cost-intensive.

Another method makes use of the determination of mass and concentration of substances in which the distribution volume V is resulting quasi as a by-product from the mass and the concentration of the sought substance according to $V=m/c$, with m being the mass in g and c being the concentration in g/ml.

From EP 1 037 681 B1 the determination of the plasma concentration via the dialysis fluid concentration is known. V is determined by means of the total mass of urea in the patient.

From EP 0 986 410 B1 the calculation of the total body mass of a dissolved substance in a distribution volume is known.

Furthermore, from DE 698 34 034 T2 an apparatus for calculating a total body mass of a dissolved substance in a fluid volume is known.

Another method for assessing the dehydration result during treatment is based on monitoring the relative blood volume, in particular after completion of the therapy. This is described, inter alia, in Lopot et al.: "Continuous blood volume monitoring and dry weight assessment", J Ren Care 2007 April-June; 33(2) 52-8, and Rodriguez et al.: "Assessment of dry weight by monitoring changes in blood volume during hemodialysis using Crit-Line", Kidney International (2005) 68, 854-861.

It is a drawback of the bioimpedance measurement that a specific measuring technology is required which is not integrated in the dialysis machine. When calculating the concentration or mass of the elutriated substances, the total mass of the substances dissolved in the fluid volume of the body must be included. The total mass in the body is a parameter which is difficult to access, however.

SUMMARY OF THE INVENTION

It is an object of the invention to provide an apparatus and to state a method by which the distribution volume of urea in the body of the patient can be reliably assessed and the course and the result of dialysis can be judged.

This object is achieved by the apparatus according to claim 1 and the method according to claim 11. Preferred embodiments of the invention are the subject matter of the respective subclaims.

Aspects of the invention are based on the consideration that when the dialysis dose D, the degree of purification ("clearance") K and the dialysis duration t are known the sought distribution volume can be easily calculated from the equation $$D=K*t/V$$

wherein D is the dialysis dose [without dimension], K is the degree of purification [ml/min], V is the volume to be purified [ml] and t is the dialysis duration [min]. The degree of purification K will in the following also be referred to as "clearance" or clearance factor.

This calculation can be performed especially "online", i.e. during therapy, so that at any point in time the urea distribution volume can be established. The dialysis dose $D=K*t/V$ can be established "online" or "quasi online" by the methods being currently known and used. The methods available for this purpose are the determination of D by conductivity measurement, the determination of D by chemical reactions (urease), the determination of D by optical absorption measurements or the determination of D by taking blood samples.

This list of methods for determining the dialysis dose D is not complete, further methods can be employed which enable determination of the dialysis dose D on the aforementioned conditions.

The apparatus according to aspects of the invention for determining a distribution volume of at least one uremic substance in a dialysis patient is provided with:
- a dialyzer for withdrawing the at least one substance from a body fluid flowing through the dialyzer, wherein the at least one substance withdrawn is disposed of through dialysis fluid equally flowing through the dialyzer,
- optionally, a flow rate measuring system for detecting a flow rate of the dialysis fluid through the dialyzer,
- a dialysis fluid measuring system for detecting at least one dialysis fluid parameter that depends on the at least one substance in the dialysis fluid, and wherein
- at least one computer is provided for establishing a dialysis dose based on the dialysis fluid parameter and for establishing the distribution volume taking a clearance factor (i.e. a degree of purification) and dialysis duration into account.

Preferred embodiments of the apparatus according to aspects of the invention include as further features, either individually or in combination, that
- the computer establishes the dialysis dose based on measured optical extinction of the dialysis fluid;
- the computer establishes the dialysis dose based on measured conductivity of the dialysis fluid;
- the computer establishes the dialysis dose based on a detected chemical reaction (urease);
- the computer establishes the dialysis dose as a function of the dialysis fluid parameter at a first time t1 and at least at a second time t2;
- the computer establishes the dialysis dose as mean value of at least two dialysis dose values;
- the computer establishes the dialysis dose as a function of the dialysis fluid parameter and of a fluid withdrawal of the dialysis patient;
- the dialysis fluid measuring system detects the dialysis fluid parameter and the flow rate measuring system detects the fluid withdrawal at least at a first time t1 and a second time t2 and the computer establishes the distribution volume by comparing the dialysis fluid parameters, the fluid withdrawal and the time interval between t1 and t2;
- the computer weights the values for the dialysis fluid parameter and the fluid withdrawal at the at least first and second times with a respective predetermined value.

The method according to aspects of the invention for determining a distribution volume of at least one uremic substance in a dialysis patient comprises the steps of:
- withdrawing the at least one substance from a body fluid with a dialyzer through which the body fluid flows and disposing of the at least one substance with a dialysis fluid equally flowing through the dialyzer,
- optionally detecting a flow rate of the dialysis fluid through the dialyzer with a flow rate measuring system,
- detecting at least one dialysis fluid parameter that depends on the at least one substance in the dialysis fluid with a dialysis fluid measuring system,
- establishing a dialysis dose based on the dialysis fluid parameter with at least one computer and establishing the distribution volume based on the dialysis dose taking a clearance factor and dialysis duration into account with the computer.

Preferred embodiments of the method according to aspects of the invention include as further features, either individually or in combination, that
- the dialysis dose is established with the computer based on measured optical extinction of the dialysis fluid;
- the dialysis dose is established with the computer based on measured conductivity of the dialysis fluid;
- the dialysis dose is established with the computer based on a detected chemical reaction (urease);
- the dialysis dose is established with the computer as a function of the dialysis fluid parameter at a first time t1 and at least at a second time t2;
- the dialysis dose is established with the computer as a mean value of at least two dialysis dose values;
- the dialysis dose is established with the computer as a function of the dialysis fluid parameter and of a fluid withdrawal of the dialysis patient;
- the dialysis fluid parameter is detected with the dialysis fluid measuring system and the fluid withdrawal is detected with the flow rate measuring system at least at a first time t1 and a second time t2 and the dialysis dose is established with a computer by comparing the dialysis fluid parameter, the fluid withdrawal and the time interval between t1 and t2;
- the values for the dialysis fluid parameter and the fluid withdrawal are weighted with the computer at the at least a first time and a second time with a respective predetermined value.

The invention offers the advantage, inter alia, that by the instantaneous, so called "online" determination of the dialysis dose D at any time during therapy the current urea distribution volume of the patient can be determined. Apart from monitoring parameter variations during therapy, moreover the values can be analyzed at the beginning and the end of therapy so as to characterize the variations in the time free from dialysis. Moreover, no additional measuring setup is required and the problem of the total mass of dissolved substances which is difficult to access is avoided.

Further features and advantages of the invention will be evident from the following description of preferred embodiments of the invention.

The determination of the urea distribution volume according to aspects of the invention relates to the fact that the dialysis dose D as well as the so called clearance of the dialyzer K and the duration of dialysis and, respectively, the time interval or the measuring period t are known. The clearance can be determined without delay during dialysis or can be read out of a memory.

For the determination of the urea distribution volume according to aspects of the invention it is important that the determination of the dialysis dose D manages without implied model assumptions, i.e. that especially no distribution volume is theoretically provided so as to determine the dialysis dose D.

BRIEF DESCRIPTION OF THE DRAWINGS

The invention is best understood from the following detailed description when read in connection with the accompanying drawing. Included in the schematic diagram are:

FIG. 1 is a schematic diagram of an apparatus in accordance with aspects of the invention.

DETAILED DESCRIPTION OF THE PREFERRED EMBODIMENTS

Two methods illustrating aspects of the invention are now provided.

Method 1

It is assumed that a dialysis dose D of 0.7 is present after a therapy time of 120 min. The clearance K is 285 ml/min. Thus the distribution volume V can be determined by:

$$K*t/V=0.7=(0.285\ l/min*120\ min)/V$$

$$V=48.9\ l.$$

The longer the measuring period t, the less the clearance K can be assumed to be constant. Assuming a variation of the clearance K during the measuring period t, this can be compensated by forming a mean value over the measuring period t.

The dialysis usually is a combination of hemodialysis and hemofiltration during which fluid is also withdrawn from the patient via the dialyzer. This means that during the measuring period t the distribution volume V of the uremic substances varies due to the withdrawal of fluid, which falsifies the result of the foregoing calculation. This can be compensated by minimizing the measuring period t and thus the fluid withdrawal being neglected. If it is no longer possible to neglect the fluid withdrawal, the fluid withdrawal UF (ultrafiltration) has to be taken into account in the calculation. Then the foregoing equation is modified as follows:

$$K*t/(0.5*[V1+\{V1-UF\}])=0.7=(0.285\ l/min*120\ min)/(V1-0.5*UF)$$

$$V1=48.9\ l+0.5*UF$$

or $$K*t/(0.5*[V2+\{V2-UF\}])=0.7=(0.285\ l/min*120\ min)/(V2+0.5*UF)$$

$$V2=48.9\ l-0.5*UF.$$

V1 is the volume at the beginning of the measuring period; V2 is the volume at the end of the measuring period. When V2 is determined at the end of therapy, it corresponds to the distribution volume present in the case of dry weight and can be used as a reference variable.

In a variant of method 1, in the case of instantaneous determination of the dialysis dose D the quotient K/V can also be directly established. This quotient can equally be used for determining the urea distribution volume. This results in the following two equations for determining the distribution volume V:

$$K/V=0.0058\ l/min=(0.285\ l/min)/V$$

$$V=49.1\ l.$$

Method 2

From a dialysis fluid parameter from which the dialysis dose is established an equation system including two equations can be formed by repeated take-up at an interval of several minutes. Formally the clearance K and the distribution volume V are deemed to be unknowns in both equations. As the body volume of the patient does not vary, apart from the withdrawal by ultrafiltration, and the clearance K is assumed to be constant in said period of time, these unknowns are identical in both equations. Hence the distribution volume V can be determined by taking up two measuring points for the value for the dialysis dose D. The unknown K is eliminated by insertion and V is determined by solving. X and Y constitute measuring values for the dialysis dose D:

$$K*t1/V1=X \quad \text{(i)}$$

$$K*t2/V2=Y \quad \text{(ii)}$$

$$\Rightarrow Y*(V2/V1)*(t1/t2)=X$$

with $V2=V1-UFR*\Delta t$, wherein $\Delta t=|t1-t2|$. UFR in this case is the ultrafiltration rate expressed in ml/min established with the flow rate measuring system and t is the time expressed in min. The flow rate measuring system can have any form and configuration. For example, it can be an invasive or non-invasive flowmeter. It is also sufficient to use the delivery pump itself as flow rate measuring system from which the volume delivered per time can be established.

By transposing the equations it follows:

$$\Rightarrow Y*t1/t2*V1-Y*t1/t2*UFR*\Delta t-X*V1=0$$

$$V1=((Y*t1/t2)/(t1/t2*Y-X))UFR*\Delta t.$$

In order to increase the accuracy of the calculation and to render the determination of the urea distribution volume independent of variations of the measuring signal, instead of two equations also plural equations can be used at times t1 ... tn. The times t1 ... tn preferably are not too widely spaced so that the clearance K can be assumed to be constant. The urea distribution volume is established on the basis of all combinations of the equations 1 ... n. Then the results are averaged, preferably weighted, so as to arrive at a final value V for the urea distribution volume.

In a variant of the method 2 the distribution volume V is established making use of the quotient K/V. When the quotient K/V is determined at two different points in time which are not too widely spaced, however, the body distribution volume V can be calculated with the aid of the values A and B taking the ultrafiltration into account. The times t1 and, respectively, t2 only have to be used for determining the amount of fluid withdrawn. This is illustrated in the following equations (iii) and (iv):

$$K/V1=A \quad \text{(iii)}$$

$$K/V2=B \quad \text{(iv)}$$

with $V2=V1-UFR*\Delta t$, wherein $\Delta t=|t1-t2|$.

By transposing the equations it follows:

$$\Rightarrow V1=(-B*UFR*\Delta t)/(A-B).$$

The following example relates to the measuring method according to equations (i) and (ii), but it can equally be implemented by the simplified method according to equations (iii) and (iv).

$$t1=20\ min;\ K*t/V=0.1000=X$$

$$t2=t1+20\ min;\ K*t/V=0.2008=Y$$

$$\Delta t=20\ min$$

$$UFR=\tfrac{1}{2}\ l/h=\tfrac{1}{120}\ l/min$$

$$\Rightarrow V1=0.2003*(20/40)/(0.2003*(20/40)-0.10000)*\tfrac{1}{120}*20=41.83\ l$$

By these embodiments of the method according to aspects of the invention, instantaneous monitoring of the course of treatment is possible for instantaneously establishing the current fluid state. Contrary to the state of the art, no additional measuring setup is required and the problem of the total mass of dissolved substances which is difficult to access is avoided. By instantaneously determining the dialysis dose D at any point in time during therapy the current urea distribution volume of the patient can be determined.

The invention is not restricted to the determination of the urea distribution volume. It is further possible to determine the distribution volumes of other substances such as uric acid, creatinine, phosphate, beta2 microglobulin, indoxylsulphate, p-cresol or p-cresylsulphate. The distribution volumes thereof deviate from the total fluid volume, which reflects their restricted distribution and diffusivity in the body. The knowledge of these distribution volumes primarily does not serve for determining the fluid state of the patient. However, it may serve for better describing the purifying process of the respective substance and especially the substance-specific behavior inside the body and in this way for more specifically optimizing the treatment.

The apparatus for materializing the method according to aspects of the invention by which the distribution volume of at least one uremic substance can be determined in a dialysis patient comprises the components briefly described hereinafter in accordance with the enclosed FIGURE.

A dialyzer is provided by which at least one substance can be withdrawn from a body fluid (e.g. blood) of the patient and can be disposed of through dialysis fluid. The dialyzer, i.e. especially its inlets and/or outlets, optionally can be provided with a flow rate measuring system so as to detect a flow rate of the dialysis fluid through the dialyzer. Moreover, by a dialysis fluid measuring system at least one dialysis fluid parameter is detected which is characteristic of the at least one substance in the dialysis fluid.

The dialysis dose D is established by the computer based on the dialysis fluid parameter. The computer then establishes the distribution volume based on the dialysis dose, wherein the clearance factor K and the dialysis duration t are included in the calculation as explained before.

The dialysis dose can be established with the computer in the ways listed in the following. A first way of establishing the dialysis dose is based on measuring the optical extinction of the dialysis fluid. A second way of establishing the dialysis dose is based on the measuring the conductivity of the dialysis fluid. A third way of establishing the dialysis dose is based on the detection of an appropriate chemical reaction (urease).

In order to improve the accuracy and the reliability of the volume determination the dialysis fluid parameter can be repeatedly detected and based thereon the dialysis dose can be repeatedly established, i.e. at a first time t1 and at least at a second time t2. Of course, further measurements can be carried out. The dialysis dose is then established as mean value of the dialysis doses from the at least two dialysis fluid parameter values.

Irrespective of the repeated detection of the dialysis fluid parameters, when determining the dialysis dose also the fluid withdrawal of the dialysis patient can be taken into account. For this purpose, an appropriate output signal UF or UFR of the flow rate measuring system of the dialyzer is included in the calculation. This output signal, too, can be detected at least at a first time t1 and a second time t2 and then the dialysis dose is established, as afore-explained, by comparing the dialysis fluid parameter, the fluid withdrawal and the time interval between t1 and t2.

In all calculations based on the repeated detection of the dialysis fluid parameters, especially in the last-mentioned way of determining the distribution volume, however, the values for the dialysis fluid parameters and the fluid withdrawal are weighted at the at least first and second times preferably with a respective predetermined value.

Summing up, the present invention relates to an apparatus and a method for determining a distribution volume of at least one uremic substance in a dialysis patient, comprising:
a dialyzer,
optionally, a flow rate measuring system for detecting the flow rate of dialysis fluid through the dialyzer,
a dialysis fluid measuring system for detecting at least one dialysis fluid parameter that depends on the at least one substance in the dialysis fluid and a computer for establishing a dialysis dose based on the dialysis fluid parameter and for establishing the distribution volume based on the dialysis dose taking a clearance factor and a dialysis duration into account.

The computer for establishing the dialysis dose and the distribution volume can be a single computer but can as well consist of plural computers. Moreover, the computer(s) can be integrated in the dialysis fluid measuring system.

Summing up, the present invention relates to an apparatus and a control method for determining a distribution volume of at least one uremic substance in a dialysis patient, comprising:
a dialyzer,
optionally, a flow rate measuring system for detecting the flow rate of dialysis fluid through the dialyzer,
a dialysis fluid measuring system for detecting at least one dialysis fluid parameter that depends on the at least one substance in the dialysis fluid, and
a computer for establishing a dialysis dose based on the dialysis fluid parameter and for establishing the distribution volume based on the dialysis dose taking a clearance factor and dialysis duration into account.

The invention claimed is:
1. An apparatus for determining a distribution volume of at least one uremic substance in a dialysis patient, comprising:
   a dialyzer for withdrawing the at least one uremic substance from a body fluid, the dialyzer adapted for dialysis fluid flowing through the dialyzer to dispose of the at least one withdrawn substance;
   a dialysis fluid measuring system for detecting at least one dialysis fluid parameter that depends on the at least one uremic substance in the dialysis fluid; and
   at least one computer configured to:
      establish a dialysis dose (D) based on the at least one dialysis fluid parameter, and
      establish the distribution volume based on the established dialysis dose (D) taking a known clearance factor (K) and a known dialysis duration (t) into account;
   wherein:
      the establishment of the dialysis dose (D) is made without implied model assumptions, wherein no distribution volume Is theoretically provided to determine the dialysis dose (D);
      a fluid withdrawal (UF, ultrafiltration) is taken into account in a calculation $K*t/(0.5*[V1+\{V1-UF\}])$, wherein V1 Is the volume at a beginning of a measuring period; and
      a current urea distribution volume of the dialysis patient can be determined by instantaneously determining the dialysis dose (D) at any point in time during a therapy.

2. The apparatus according to claim 1, further comprising:
a flow rate measuring system for detecting a flow rate of the dialysis fluid through the dialyzer.

3. The apparatus according to claim 1, wherein the computer establishes the dialysis dose based on measured optical extinction of the dialysis fluid.

4. The apparatus according to claim 1, wherein the computer establishes the dialysis dose based on measured conductivity of the dialysis fluid.

5. The apparatus according to claim 1, wherein the computer establishes the dialysis dose (D) based on a detected chemical reaction.

6. The apparatus according to claim 5, wherein the detected chemical reaction is a urease test.

7. The apparatus according to claim 1, wherein the computer establishes the dialysis dose (D) response to the dialysis fluid parameter at a first time, t1, and at least at a second time, t2.

8. The apparatus according to claim 7, wherein the computer establishes the dialysis dose (D) as mean value of at least two dialysis dose values.

9. The apparatus according to claim 2, wherein the computer establishes the dialysis dose (D) in response to the at least one dialysis fluid parameter and to the fluid withdrawal (UF) of the dialysis patient, wherein the fluid withdrawal (UF) is established based on a flow rate of the dialysis fluid through the dialyzer.

10. The apparatus according to claim 1, wherein the computer establishes the dialysis dose (D) based on comparison between a dialysis fluid inlet flow and a dialysis fluid outlet flow.

11. The apparatus according to claim 9, wherein the dialysis fluid measuring system detects the dialysis fluid parameter and the flow rate measuring system detects the fluid withdrawal (UF) at least at a first time, t1, and a second time, t2, and the computer establishes the distribution volume by comparison of the dialysis fluid parameter, the fluid withdrawal (UF) and a time interval between t1 and t2.

12. The apparatus according to claim 11, wherein the computer weights the values for the dialysis fluid parameter and the fluid withdrawal (UF) at the at least first time t1 and the second time t2 with a respective predetermined value.

13. A machine control method for machine-side determination of a distribution volume of at least one uremic substance in a dialysis patient comprising the control steps of:
withdrawing the at least one uremic substance from a body fluid with a dialyzer and disposing of the at least one uremic substance using a dialysis fluid flowing through the dialyzer;
detecting at least one dialysis fluid parameter that depends on the at least one uremic substance in the dialysis fluid with a dialysis fluid measuring system;
establishing a dialysis dose (D) based on the at least one dialysis fluid parameter with at least one computer; and
establishing the distribution volume based on the established dialysis dose (D) with the at least one computer taking a known clearance factor (K) and a known dialysis duration (t) into account; wherein:
the establishment of the dialysis dose (D) is made without implied model assumptions, wherein no distribution volume is theoretically provided to determine the dialysis dose (D);
a fluid withdrawal (UF, ultrafiltration) is taken into account in a calculation $K*t/(0.5*[V1+\{V1-UF\}])$, wherein V1 is the volume at a beginning of a measuring period; and
a current urea distribution volume of the dialysis patient can be determined by instantaneously determining the dialysis dose (D) at any point in time during a therapy.

14. The method according to claim 13 further comprising the control step of:
detecting a flow rate of the dialysis fluid with a fluid rate measuring system.

15. The method according to claim 13, wherein the dialysis dose (D) is established based on a measured optical extinction of the dialysis fluid, a measured conductivity of the dialysis fluid, or a detected chemical reaction by the at least one computer.

16. The method according to claim 15, wherein the detected chemical reaction is a urease test.

17. The method according to claim 13, wherein the dialysis dose (D) is established by the at least one computer in response to the at least one dialysis fluid parameter at a first time, t1, and at least at a second time, t2.

18. The method according to claim 17, wherein the dialysis dose (D) is established as mean value of at least two dialysis dose values by the at least one computer.

19. The method according to claim 14, wherein the dialysis dose (D) is established by the at least one computer in response to the at least one dialysis fluid parameter and to the fluid withdrawal (UF) of the dialysis patient, wherein fluid withdrawal (UF) is established based on the flow rate of the dialysis flow through the dialyzer.

20. The method according to claim 13, wherein the dialysis dose (D) is established based on comparison between a dialysis fluid inlet flow and a dialysis fluid outlet flow.

21. The method according to claim 19, wherein the at leas one dialysis fluid parameter is detected by the dialysis fluid measuring system and the fluid withdrawal (UF) is detected by the fluid rate measuring system at least at a first time, t1, and a second time, t2, and the distribution volume is established by the at least one computer by comparison of the dialysis fluid parameters, the fluid withdrawal (UF), and the time interval between t1 and t2.

22. The method according to claim 21, wherein the values for the at least one dialysis fluid parameter and the fluid withdrawal (UF) are weighted by the at least one computer at the at least first time t1 and the second time t2 with a respective predetermined value.

* * * * *